(12) United States Patent
Weber

(10) Patent No.: US 8,915,951 B2
(45) Date of Patent: Dec. 23, 2014

(54) SELF-EXPANDABLE STENT WITH A CONSTRICTIVE COATING AND METHOD OF USE

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1039 days.

(21) Appl. No.: 12/368,459

(22) Filed: Feb. 10, 2009

(65) Prior Publication Data

US 2009/0204196 A1 Aug. 13, 2009

Related U.S. Application Data

(60) Provisional application No. 61/027,608, filed on Feb. 11, 2008.

(51) Int. Cl.
| | |
|---|---|
| A61F 2/06 | (2013.01) |
| A61L 31/14 | (2006.01) |
| A61L 31/10 | (2006.01) |
| A61F 2/97 | (2013.01) |
| A61F 2/07 | (2013.01) |
| A61B 17/32 | (2006.01) |

(52) U.S. Cl.
CPC ........... *A61F 2/97* (2013.01); *A61F 2250/0067* (2013.01); *A61L 31/14* (2013.01); *A61L 31/10* (2013.01); *A61F 2/07* (2013.01); *A61B 2017/32004* (2013.01)
USPC ...................................................... 623/1.12

(58) Field of Classification Search
CPC ....... A61F 2/2427; A61F 2/2436; A61F 2/95; A61F 2/954; A61F 2/962; A61F 2/966; A61F 2/97; A61F 2/07; A61F 2002/072; A61F 2002/30003
USPC .................. 606/108, 153, 200; 623/1.1–2.11, 623/23.72–23.74; 600/566, 567
See application file for complete search history.

(56) References Cited

U.S. PATENT DOCUMENTS

| | | | | |
|---|---|---|---|---|
| 5,919,225 | A * | 7/1999 | Lau et al. ...................... | 606/198 |
| 6,629,992 | B2 * | 10/2003 | Bigus et al. ................... | 623/1.12 |
| 7,294,146 | B2 * | 11/2007 | Chew et al. ................... | 623/1.12 |
| 7,306,677 | B2 | 12/2007 | Robida | |
| 7,347,868 | B2 * | 3/2008 | Burnett et al. ............... | 623/1.11 |
| 8,088,154 | B2 * | 1/2012 | Hoffman et al. ............. | 623/1.11 |
| 2007/0219612 | A1 * | 9/2007 | Andreas et al. .............. | 623/1.11 |

* cited by examiner

*Primary Examiner* — Melanie Tyson
(74) *Attorney, Agent, or Firm* — Fish & Richardson P.C.

(57) ABSTRACT

The present invention provides a system and method for providing a coating on a self-expandable medical device, such as a stent, while avoiding the issues relating to coating damage from the delivery sheath during loading and deployment. In one embodiment, the present invention includes a constrictive coating that acts as a constrictive sheath for the stent. A cutting mechanism is mounted on the end of the delivery tube such that when the stent with the constrictive coating exits the delivery tube, the constrictive coating is cut. This releases the constriction retaining the sheath, and the stent self-expands, pressing the cut portions of the coating against the lumen wall.

23 Claims, 7 Drawing Sheets

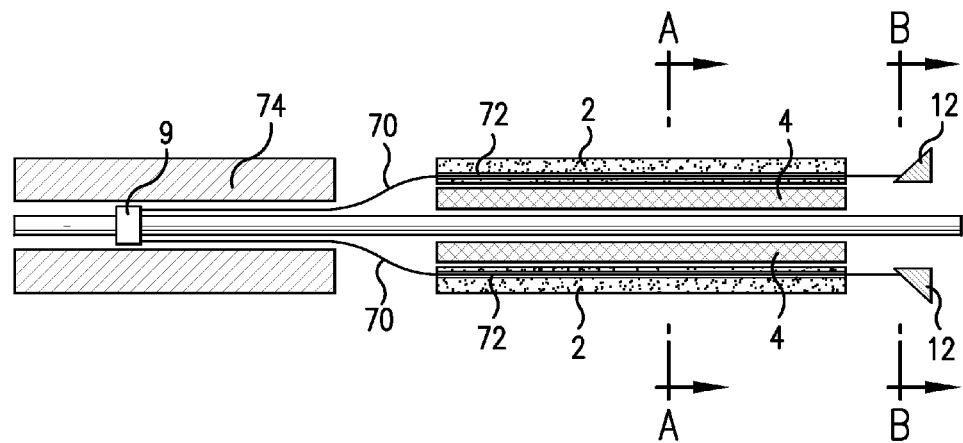
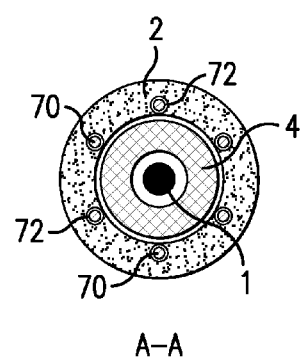 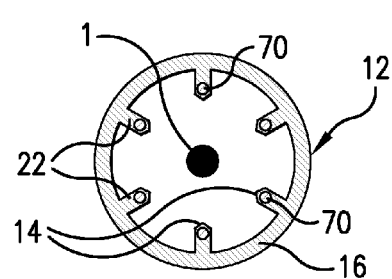
FIG.6a
FIG.6b  FIG.6c

SELF-EXPANDABLE STENT WITH A CONSTRICTIVE COATING AND METHOD OF USE

CROSS REFERENCE TO RELATED APPLICATION

The present application claims priority to U.S. provisional application Ser. No. 61/027,608 filed Feb. 11, 2008, the disclosure of which is incorporated herein by reference in its entirety.

FIELD OF INVENTION

The present invention relates to coated self-expanding stents and methods of delivering such stents.

BACKGROUND

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with a therapeutic agent to be locally delivered. The coating on medical devices may provide for controlled release, which may include long-term or sustained release, of a bioactive material. Coatings can be applied to medical devices by processes such as dipping, spraying, vapor deposition, plasma polymerization, spin-coating and electrodeposition.

Aside from facilitating localized drug delivery, medical devices may be coated with materials to provide beneficial surface properties. For example, medical devices are often coated with radiopaque materials to allow for fluoroscopic visualization while placed in the body. It is also useful to coat certain devices to achieve enhanced biocompatibility and to improve surface properties such as lubriciousness.

A conventional self-expandable (SE) stent has an expanded form when not constrained. To deliver the stent to the desired location in the body, the stent typically is compressed radially and loaded into a delivery system. A typical delivery system consists of an outer tubular sheath retaining the compressed stent. The delivery system is tracked to the region of a vessel being stented. The stent is then released from its compressed state by retracting the sheath and/or pushing the stent out of the sheath. When released from the constraint of the sheath, the stent self-expands back to its expanded form to scaffold the vessel wall.

BRIEF DESCRIPTION

The present invention provides a system and method for providing and deploying a self-expandable medical device, such as a stent, without damaging the coating.

During loading and deployment of self-expandable stents, there may be significant friction between the stent outer surface and the delivery sheath. Because the self-expandable stent has a tendency to want to expand to its relaxed state, the stent presses radially outward against the inner surface of the sheath. Thus, when the stent is being loaded into and/or deployed out of the sheath, the frictional forces may be significant. Additionally, longer stents may have higher frictional forces. When the self-expandable stents have a coating on the outer surface, these forces may damage the coating. A coating on the outer surface of the self-expandable stent that is in contact with the inner surface of a delivery sheath is subject to high shear forces during both loading and deployment. Therapeutic agent coatings for medical devices may be relatively soft, for example consisting of a mixture of biodegradable or biostable polymers and drugs, or solely drugs. Particularly, such a soft coating can easily be stripped or damaged by contact with a delivery sheath during loading or deployment.

The present invention provides a system and method for providing a coating on a self-expandable medical device, such as a stent, while avoiding the issues relating to coating damage from the delivery sheath during loading and deployment. In one embodiment, the present invention comprises a constrictive coating that acts as a constrictive sheath for the stent during delivery and serves as a stent coating upon deployment. During delivery, the coating constrains the stent and is not pressed by the stent's expansion forces against the inner surface of the delivery tube. Thus, there is limited frictional force between the delivery tube surrounding the stent and the coating on the stent. A cutting mechanism is mounted on the end of the delivery tube such that when the stent with the constrictive coating exits the delivery tube, the constrictive coating is cut. This releases the constriction retaining the stent and the stent self-expands, pressing the cut portions of the coating against the lumen wall. A constrictive coating in accordance with one embodiment of the invention may have one or more of the following advantages: (1) being able to extend the coating proximally and/or distally of the stent, (2) assuring the coating is only abluminal, and/or (3) controlling the amount of therapeutic agent to be delivered to the body lumen in the coating. Additionally, the delivery tube can be much thinner than traditional delivery tubes, since it does not have to oppose the outward radial force of the stent, resulting in a more flexible system. Also, because the delivery tube can be thinner, the overall profile can be similar to or even smaller than existing systems, despite the presence of the constrictive coating.

BRIEF DESCRIPTION OF THE DRAWINGS

FIG. 1b and FIG. 1c show two different cross-sectional views of the stent deployment system of FIG. 1a.

FIG. 2a shows the stent deployment system of FIG. 1a during deployment of the stent and FIG. 2b and FIG. 2c show two different cross-sectional views of the stent deployment system of FIG. 2a.

FIG. 3a shows the stent and coating and FIG. 3b shows the stent and coating loaded in a delivery tube.

FIG. 4a shows an embodiment of a stent with a constrictive coating that includes shape memory material and FIG. 4b shows a cross-sectional view of the stent with a constrictive coating of FIG. 4a.

FIG. 6a shows an embodiment of a stent deployment system prior to deployment of the stent including the blades mounted on wires, and FIG. 6b and FIG. 6c show two different cross-sectional views of the stent deployment system of FIG. 6a.

FIG. 8b shows a cross-sectional view of the stent deployment system of FIG. 8a.

DETAILED DESCRIPTION

Figure 1A:
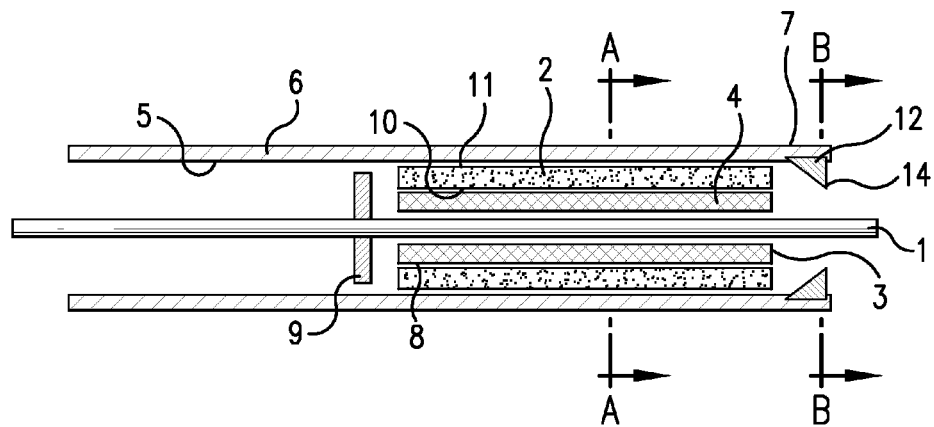
FIG. 1a shows an embodiment of the stent deployment system prior to deployment of the stent.
Figure 1B:
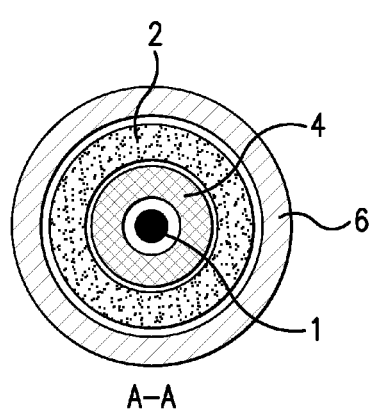
Figure 1C:
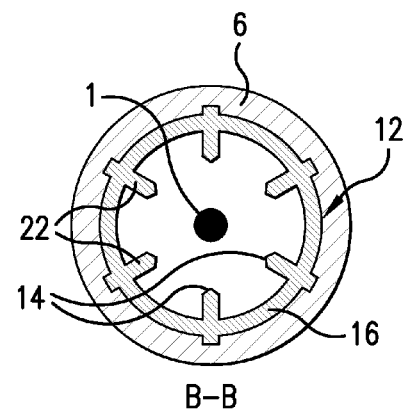

FIGS. 1a-1c and 2a-2c show an embodiment of a stent deployment system for deploying a self-expandable stent with a coating. The system comprises a constrictive coating 2 and a self-expandable stent 4, both housed within a delivery tube 6. Since the constrictive coating 2 prevents the self-expandable stent 4 from expanding to its unconstrained form, the stent 4 does not press the coating 2 against the delivery tube 6 with great force. In this embodiment, there is a small clearance space between the coating 2 and the delivery tube 6. Furthermore, if the coating 2 does abut the delivery tube 6, there will be little to no shear forces that could cause damage to the coating 2. A cutting mechanism 12 in the form of an annular ring 16 of blades 22 is mounted at the distal end 7 of the delivery tube 6. A guidewire 1 is used for delivering the stent deployment system to the implantation site within the body. In this embodiment, the guidewire 1 has a proximal stop 9, to assist in the delivery of the stent 4 from the delivery tube 6.

For clarity, the stent 4 is shown schematically both in its structure and in its relation to the sheath. The stent may take any suitable configuration, and many such configurations are known in the art. It will be appreciated that because a self-expandable stent 4 has a tendency to expand to its unconstrained state, the outer surface 8 of the stent 4 ordinarily presses outward against the inner surface 10 of the constrictive coating 2. For clarity of illustration, the figures show a small space between the outer surface 8 of the stent 4 and the inner surface 10 of the constrictive coating 2, although it will be understood that in practice these surfaces will ordinarily be abutting.

Figure 2A:
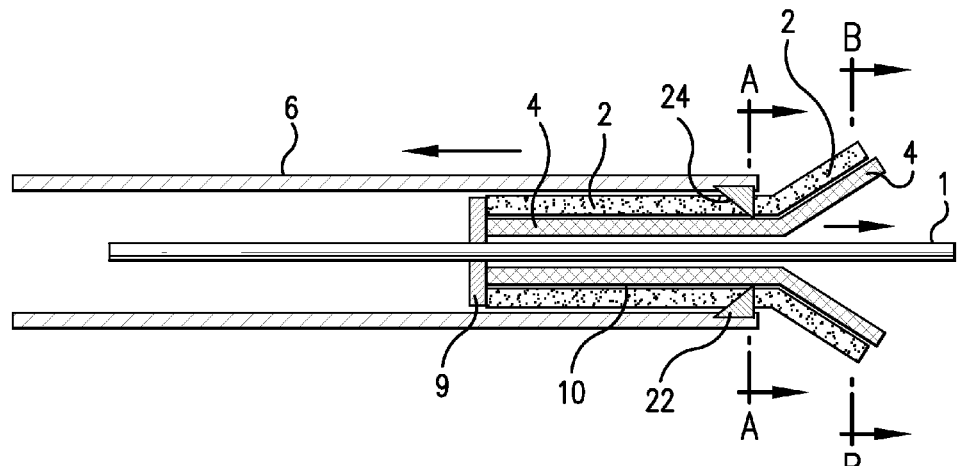
Figure 2B:
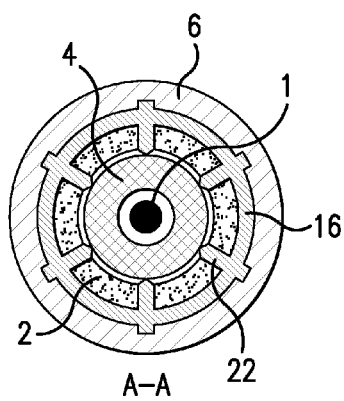
Figure 2C:
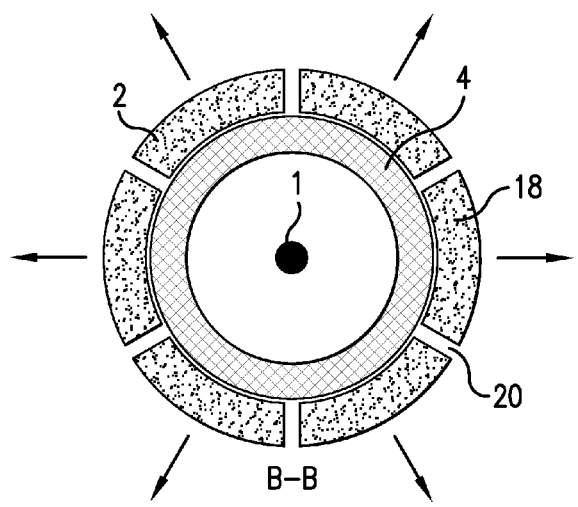

As shown in FIG. 2a, the stent 4 is deployed from the delivery tube 6 by retracting the tube 6 so the stent abuts proximal stop 9, or by pushing the stent 4 out of the delivery tube 6. During deployment, the stent 4 moves together with the constrictive coating 2, relative to the inner surface 5 of the delivery tube 6. Beginning at the distal end 3 of the stent 4, the stent 4 exits the delivery tube 6 through the opening at the distal end 7 of the delivery tube 6. The outer surface 11 of constrictive coating 2 on the stent 4 then contacts the annular inner surface 14 of the cutting mechanism 12, allowing the ring 16 of blades 22 to cut through the constrictive coating 2 during stent deployment.

The ring 16 of blades 22 includes a plurality of individual blades 22 arranged around the circumference of the delivery tube 6. Alternatively, the blades 22 can each be separately mounted or embedded into the material of the delivery tube 6. Although any number of blades can be used, in this illustrated embodiment, six blades are used. In one embodiment, the blades 22 are metal, however the blades can be composed of ceramic, hard thermoset polymers, diamond, or any other suitable material. The blades are preferably biocompatible, but this is not a requirement as they will not be implanted in the body. Each blade 22 has a cutting edge 24 that faces proximally into the center of the delivery tube 6 to cut the constrictive coating 2 into a plurality of longitudinal strips 18. The diameter of the circle formed by the tips of the blades 22 extending into the center of the tube 6 is less than the outer diameter of the constrictive coating 2 and about equal to the inner diameter of the constrictive coating 2, thus allowing the blades 22 to fully cut through the constrictive coating 2. If the blades do touch the stent, the stent will not be cut or damaged as the force applied is not large enough.

As the stent 4 exits the distal side of the cutting mechanism 12, because the constrictive coating has been slit, the stent 4 is no longer constrained by the constrictive coating 2. Thus, the stent 4 expands to its unconstrained shape to scaffold the body lumen, with the cut longitudinal strips of coating 18 lying between the body lumen and the stent 4. Due to the expansion of the stent 4, there may be small spaces 20 between the longitudinal strips of coating 18, where the stent 4 is bare.

Figure 3A:
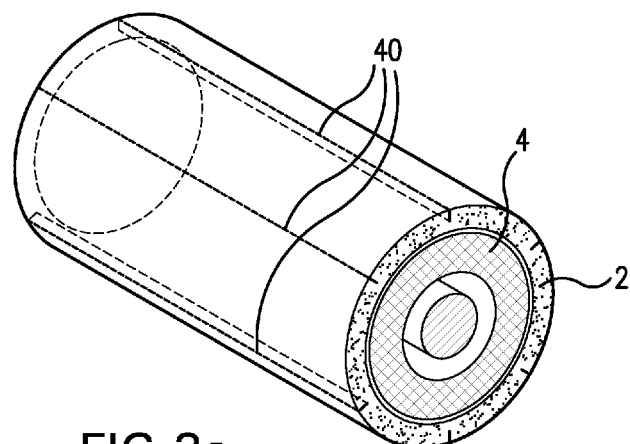
FIGS. 3a and 3b show an alternative embodiment with perforations in the constrictive coating.
Figure 3B:
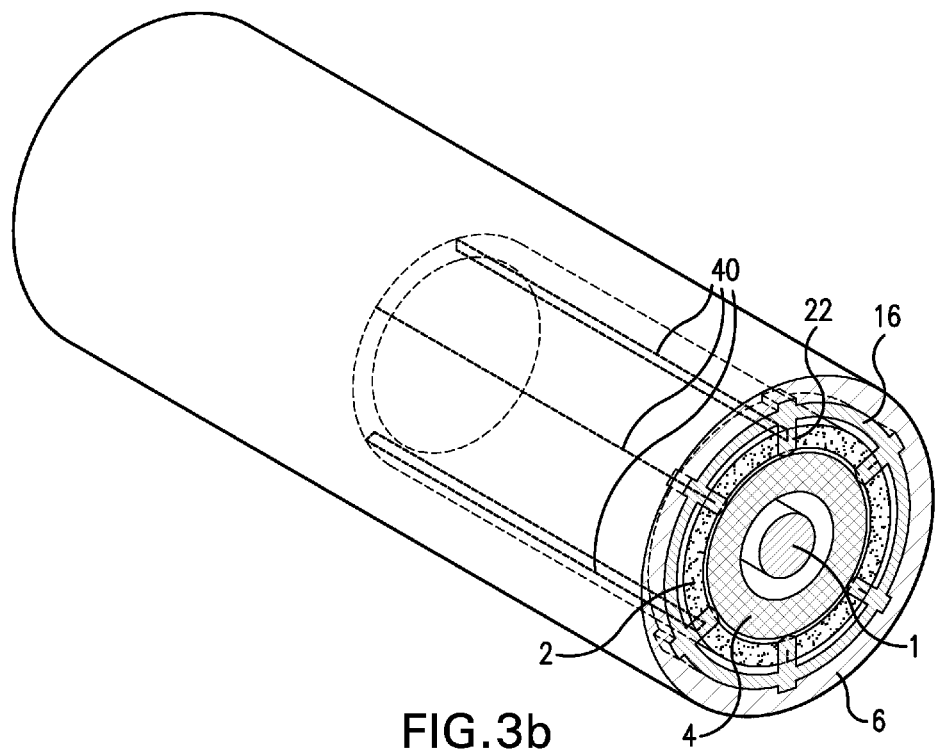

As shown in FIGS. 3a and 3b, the coating 2 may include perforations 40 to assist in cutting the constrictive coating 2 into longitudinal strips 18. Such perforations 40 may be in the form of a row of holes or a slit extending only partially through the thickness of the coating. The perforations 40 can be formed by a laser or other suitable mechanism prior to mounting the stent 4 and constrictive coating 2 within the delivery tube 6. To ensure that the perforations 40 are aligned with the blades 22 during delivery, the constrictive coating 2 can include markings on the distal end.

Figure 4A:
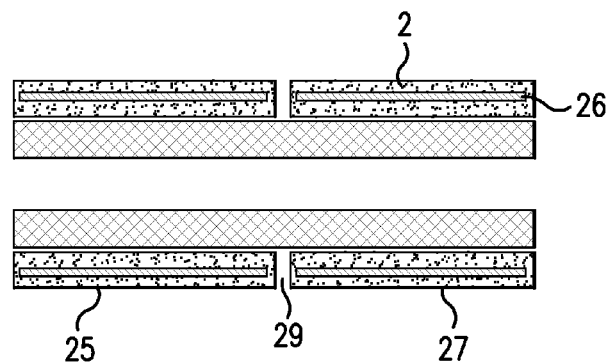
Figure 4B:
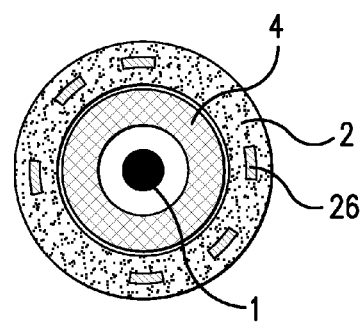
Figure 4C:
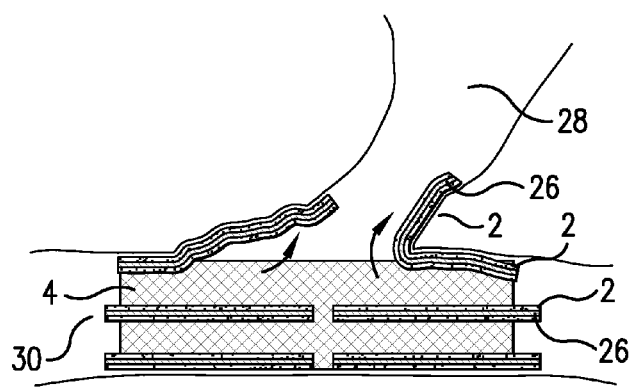
FIG. 4c shows the stent with a constrictive coating of FIG. 4a in use.

In the embodiment of FIGS. 4a-c, the coating further includes a biocompatible shape memory material, such as Nitinol. Such an embodiment is especially useful when the stent is to be placed in a body lumen with at least one bifurcation, as shown in FIG. 4c. The constrictive coating 2 includes strips of shape memory material 26 embedded within the constrictive coating 2. In one embodiment, the constrictive coating 2 is in two sections 25 and 27, of about even lengths, with a small space 29 in between. Thus, when the coating 2 is longitudinally cut by the cutting mechanism 12, the strips of shape memory material 26 return toward their unconstrained curved shape, and substantially conform to the walls of a bifurcation 28 in the body lumen, while the stent 4 remains in the primary body lumen 30, as seen in FIG. 4c. Although two sections are shown, this embodiment is merely exemplary. A different number of sections can be used, for instance, for a body lumen with multiple bifurcations.

Figure 5A:
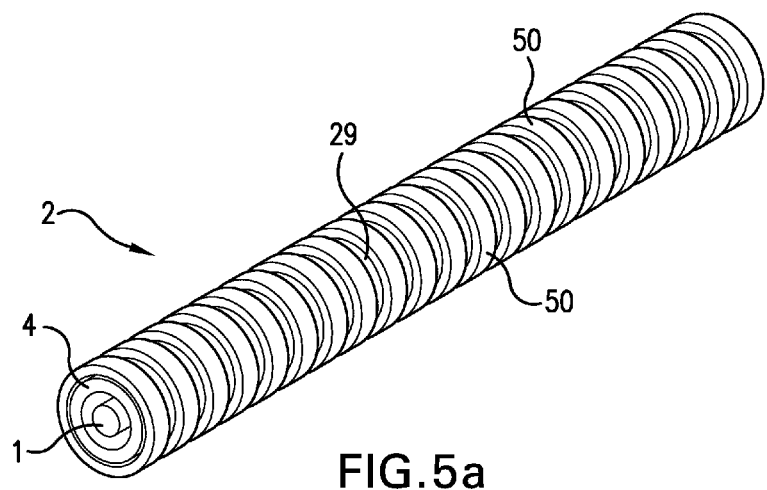
FIG. 5a shows an embodiment of the coating as a plurality of rings.
Figure 5B:
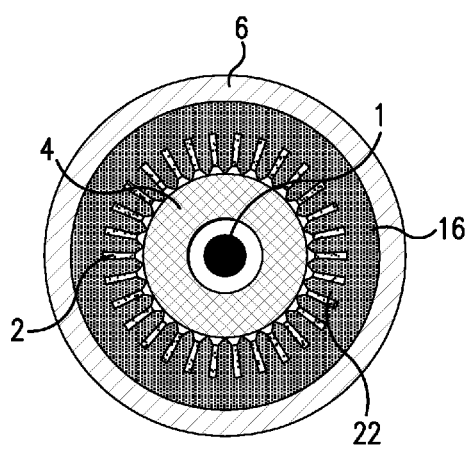
FIG. 5b shows the embodiment of FIG. 5a in a delivery tube.
Figure 5C:
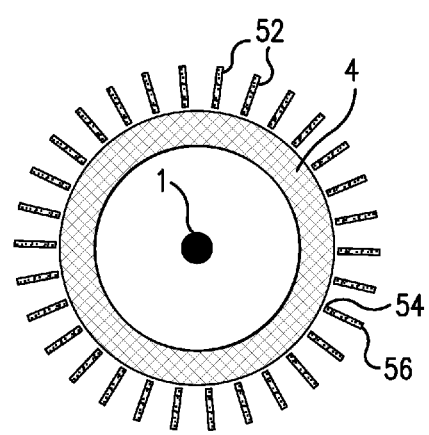
FIG. 5c shows the coating as a plurality of rings after delivery.

FIGS. 5a-c show an alternative embodiment, where the coating 2 is formed as a plurality of narrow rings 50 with small spaces 29 in between. Each ring 50 of the constrictive coating 2 can include small pieces of shape memory material 26 embedded within the coating. When the rings 50 are longitudinally cut by the cutting mechanism 12, each ring 50 is cut into a plurality of sections, for example, about 20 to 30 sections. As shown in FIGS. 5b and 5c, each section of each ring 50 forms small cilia-like extensions 52, which are attached to the stent 4 at a proximal end 54 by any suitable means, such as by adhesive, by melting the proximal end 54, or by any other known means. At least the free distal end 56 of the extension 52 is coated or embedded with a therapeutic. When the rings 50 are cut into sections, the shape memory material 26 within the extensions 52 tends to return to the unconstrained shape, extending the free distal end 56 to the walls of the body lumen.

In an alternative embodiment, such as that shown in FIGS. 6a-c, the stent need not be delivered inside of a delivery tube, because the coating holds the stent constrained for delivery. The embodiment shown in FIGS. 6a-c includes a plurality of wires 70 with a cutting mechanism 12 attached to the distal ends thereof. The proximal end of the wires 70 is mounted on a proximal stop 9 that is fixedly attached to the guidewire 1 within a stop tube 74. The cutting mechanism 12 can include a plurality of individual blades 22 mounted on an annular ring 16, adapted to cut through the constrictive coating 2. The guidewire 1 with attached wires 70 and ring 16 are moved relative to the stent 4 and coating 2 to actuate the cutting mechanism 12. For example, pulling the wires 70 proximally pulls the cutting mechanism 12 proximally through the coating 2. Once through the entire stent, the annular ring 16 comes to a halt when it abuts the stop tube 74 located proximal to the stent 4. The stop tube 74 may have about the same outer dimensions as the ring 16 to provide a smooth outer surface for removing the entire system from the body lumen. The wires 70 can be housed within channels 72 either in the constrictive coating 2, between the stent 4 and constrictive coating 2 (not shown), or on the outer surface 11 of the constrictive coating 2 (not shown). Although six wires are shown, any configuration of the wires is acceptable. The wires need not be attached to the guidewire 1 but may instead extend outside of the body or may be attached to an alternative actuation mechanism.

Figure 7:
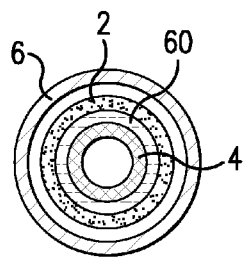
FIG. 7 shows an embodiment with a hydrogel layer.

In another embodiment, shown in FIG. 7, there is a hydrogel layer 60 between the constrictive coating 2 and the stent 4. Once the stent 4 is implanted in the body, the hydrogel layer 60 contacts fluid and swells, thereby pushing the coating 2 away from the stent and flush against the body lumen.

In another embodiment, there maybe be multiple layers of coating. The stent 4 may be coated with a first soft coating, which is then contained within the constrictive coating 2. In this embodiment, each coating layer can include a different therapeutic.

Figure 8A:
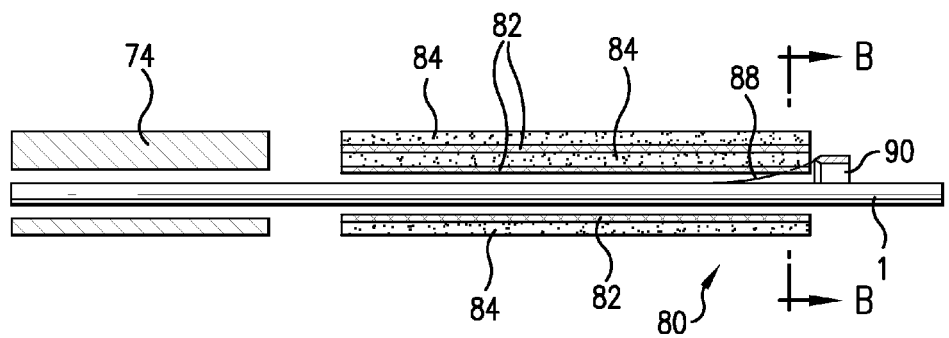
FIG. 8a shows an embodiment of a stent deployment system including a curved spiral blade.
Figure 8B:
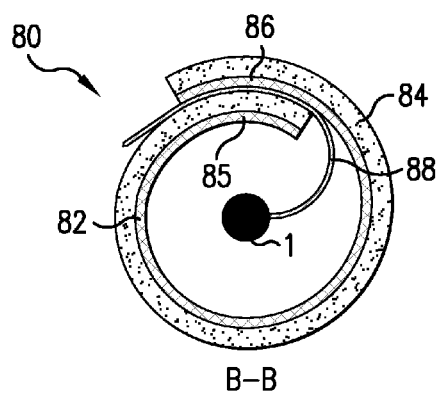

In another embodiment, shown in FIGS. 8a-b, the stent 80 can be made of a flexible shape memory sheet 82 coated with a therapeutic coating 84. The stent 80 may be formed by the sheet 82 being rolled in a cigarette-fashion with two overlapping longitudinal sides 85, 86. The two sides 85, 86 are held together where the stent wraps upon itself, which may be accomplished by bonding adhesive, melting, or any other suitable means. In this embodiment, a curved or spiral blade 88 is used to cut the coating 84 in between the two longitudinal sides 85, 86, thereby separating them and allowing the coated shape memory sheet 82 to expand and scaffold the body lumen. The spiral blade 88 may have a housing 90 mounted on the distal end of the guide wire 1, and the spiral blade 88 may be pulled relative to the stent 80 to cut the coating 84 and to thereby allow the sheet 82 to unroll. The spiral blade 88 comes to a halt when it abuts a stop tube 74 located proximal to the stent 80. The stop tube 74 may be sized to allow the blade 88 and housing 90 to sit inside the stop tube 74 during removal to provide a smooth outer surface for removing the entire system from the body lumen. Variations on this embodiment ate possible. For example, the spiral blade may be attached to and actuated by wires that are separate from the guidewire 1.

A typical stent may have a length, for example, of about 8-40mm and a wall thickness of about 80-100 μm, but other sizes are of course possible. The coating may be applied within the range of known coating thicknesses, but smaller and larger coatings are of course possible. The coating thickness can be, for example, in an amount of 0.5 μg/mm$^2$ to about 20 μg/mm$^2$, depending on the drug used, the drug dosage, and the polymer used. The coating can include a therapeutic in the amount of about 0.1 to about 10 μg/mm$^2$, but other amounts are of course possible. The cutting mechanism 12 can be mounted onto the distal end 7 of the delivery tube 6 by any conventional method, such as gluing, welding, mechanically fixing, melting the end of the delivery tube, or interference fit, or the individual blades can be embedded in the delivery tube material. The delivery tube 6 may be made of, for example, any very thin polymer material, such as nylon.

The constrictive coating may be made of a harder, sturdy material than is normally used in a medical device coating to constrict the stent and prevent the stent from expanding until the coating is cut. Exemplary materials include polymers such as PTFE, polyethylene terephthalate (PET), poly(ethylene naphthalate) (PEN) polyester available from DuPont in Wilmington, Del. under the tradename of TEONEX™, polyamides such as amorphous nylon and nylon 12 such as those available from Elf Atochem under the tradename of CRISTAMID™, polyphenylene sulfide (PPS); polyolefins such as polyethylenes and polypropylenes including low, medium and high densities such as HDPE available under the tradename of ALATHON™ from Equistar Chemicals, polyurethane, cellulose, or any combinations thereof. A biocompatible metal can further be used in combination with a polymer to impart more sturdiness to the coating. The coating may include a therapeutic agent that may be any suitable pharmaceutically acceptable agent such as a non-genetic therapeutic agent, a biomolecule, a protein, a small molecule, or cells, as further described in co-assigned U.S. Pat. No. 7,306,677, which is herein incorporated by reference in its entirety. Any of the suitable therapeutic agents may be combined to the extent that such combination is biologically compatible. The coating may be bonded to the stent, or may be in the form of a sheath or rings into which the stent is inserted.

Although the invention is described with reference to a self-expandable stent, the constrictive coating system can be used on other self-expandable medical devices. Such medical devices can be implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A system for deploying a self-expandable medical device with a coating, comprising:
   a self-expandable medical device;
   a constrictive coating on an outer surface of the medical device, said constrictive coating preventing the self-expansion of the medical device, said coating adapted to be implanted in a body lumen along with the medical device;

a delivery tube having an opening at a distal end of the tube, the self-expandable medical device and the constrictive coating housed inside the delivery tube; and at least one cutting mechanism mounted at the distal end of the delivery tube and adapted to longitudinally cut the constrictive coating as the medical device exits the delivery tube through the opening at the distal end of the delivery tube so that the longitudinally-cut coating permits self-expansion of the medical device.

2. The system of claim 1, wherein the cutting mechanism comprises plurality of blades mounted on an annular inner surface of the delivery tube.

3. The system of claim 2, wherein the blades are evenly spaced around a circumference of the delivery tube.

4. The system of claim 2, wherein the blades are unevenly distributed around a circumference of the delivery tube.

5. The system of claim 2, wherein the plurality of blades comprises two to eight blades.

6. The system of claim 2, wherein each blade includes a cutting edge that extends into a center of the delivery tube and faces proximally.

7. The system of claim 2, wherein the cutting mechanism further comprises a ring at the distal end of the delivery tube on which the plurality of blades is mounted.

8. The system of claim 1, wherein the constrictive coating is made of a material that keeps the medical device from expanding until the constrictive coating is cut by the cutting mechanism.

9. The system of claim 8, wherein the material comprises polyurethane, cellulose, or a combination thereof 10. The system of claim 1, wherein the constrictive coating further comprises a biocompatible metal.

11. The system of claim 10, wherein the biocompatible metal is a shape memory metal.

12. The system of claim 11, wherein the constrictive coating initially comprises two cylindrical sections.

13. The system of claim 12, wherein the two cylindrical sections are of approximately equal lengths.

14. The system of claim 1, wherein the constrictive coating comprises a plurality of rings, each ring having a proximal edge and a distal edge.

15. The system of claim 14, wherein the proximal edge of each ring is attached to the medical device.

16. The system of claim 1, wherein the constrictive coating is bonded to the medical device.

17. The system of claim 1, wherein the constrictive coating is a sheath into which the medical device is inserted.

18. The system of claim 1, wherein the medical device is a stent.

19. The system of claim 1, wherein the constrictive coating includes a therapeutic agent.

20. The system of claim 1, wherein the at least one cutting mechanism is fixedly mounted at the distal end of the delivery tube.

21. A method of deploying a self-expandable medical device with a coating, comprising the steps of:

using a self-expandable medical device with a constrictive coating around the medical device, said constrictive coating preventing the self-expansion of the medical device, whereby the medical device with the constrictive coating is inside a delivery tube, the delivery tube comprising an opening at a distal end of the tube, and whereby at least one cutting mechanism is on the distal end of the tube;

inserting the delivery tube containing the medical device and constrictive coating into a lumen of a patient; and deploying the medical device with the constrictive coating from the opening at the distal end of the delivery tube, thereby longitudinally cutting the constrictive coating on the medical device as the medical device passes by the cutting mechanism so that the longitudinally-cut coating allows the medical device to self-expand as it exits from the delivery tube.

22. The method of claim 21, wherein the constrictive coating comprises a shape memory material and the body lumen includes a bifurcation, and wherein when the constrictive coating is cut, cut portions of the constrictive coating change toward their unconstrained curved state to substantially conform to the walls of the bifurcation as the medical device expands.

23. A system for deploying a self-expandable medical device with a coating, comprising:

a self-expandable medical device;

a constrictive coating on an outer surface of the medical device, said constrictive coating preventing the self-expansion of the medical device, said coating adapted to be implanted in a body lumen along with the medical device;

a delivery tube having an opening at a distal end of the tube, the self-expandable medical device and the constrictive coating housed inside the delivery tube; and at least one cutting mechanism mounted at the distal end of the delivery tube and adapted to longitudinally cut only the constrictive coating as the medical device exits the delivery tube through the opening at the distal end of the delivery tube so that the longitudinally-cut coating permits self-expansion of the medical device.

* * * * *